United States Patent
Lee et al.

(10) Patent No.: US 11,285,492 B2
(45) Date of Patent: Mar. 29, 2022

(54) SCREENING METHOD FOR HIGH-EFFICIENCY BIOFUEL-PRODUCING STRAINS BY DIELECTROPHORETIC METHOD USING VERTICAL NANO-GAP ELECTRODES

(71) Applicant: KOREA INSTITUTE OF SCIENCE AND TECHNOLOGY, Seoul (KR)

(72) Inventors: Sun Mi Lee, Seoul (KR); Yong-Sang Ryu, Seoul (KR); Eui-Sang Yu, Seoul (KR); Jiwon Kim, Seoul (KR); Ja Kyong Ko, Seoul (KR); Gyeongtaek Gong, Seoul (KR); Chulki Kim, Seoul (KR); Jae Hun Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 393 days.

(21) Appl. No.: 16/393,967

(22) Filed: Apr. 25, 2019

(65) Prior Publication Data
US 2020/0188933 A1   Jun. 18, 2020

(30) Foreign Application Priority Data

Dec. 17, 2018   (KR) .................. 10-2018-0163570

(51) Int. Cl.
*B03C 5/00*      (2006.01)
*C12P 7/64*      (2006.01)
*C12P 7/649*     (2022.01)

(52) U.S. Cl.
CPC .............. *B03C 5/005* (2013.01); *C12P 7/649* (2013.01)

(58) Field of Classification Search
CPC ....... B03C 5/005; B03C 5/026; C12P 7/6427; C12P 7/649; C12Q 1/6886; C12Q 2600/154; Y02E 50/10
See application file for complete search history.

(56) References Cited

FOREIGN PATENT DOCUMENTS

| JP | 2013224947 A | 10/2013 | |
|---|---|---|---|
| JP | 2015500640 A | 1/2015 | |
| KR | 1020140091640 A | 7/2014 | |
| KR | 1020180033711 A | 4/2018 | |
| WO | WO-2009146143 A2 * | 12/2009 | ........... G01N 33/491 |
| WO | 2012121229 A1 | 9/2012 | |

OTHER PUBLICATIONS

KR1020180033711 Trans Description (Year: 2018).*
Korean Notice of Allowance for KR Application No. 10-2018-0163570 dated Jun. 29, 2020.

* cited by examiner

*Primary Examiner* — Ellen M McAvoy
*Assistant Examiner* — Chantel L Graham
(74) *Attorney, Agent, or Firm* — Cantor Colburn LLP

(57) ABSTRACT

Disclosed herein are a screening method of high-efficiency biofuel-producing strains by a dielectrophoretic method using vertical nano-gap electrodes and a producing method of biofuel from the screened strains.

19 Claims, 7 Drawing Sheets

SCREENING METHOD FOR HIGH-EFFICIENCY BIOFUEL-PRODUCING STRAINS BY DIELECTROPHORETIC METHOD USING VERTICAL NANO-GAP ELECTRODES

BACKGROUND OF THE INVENTION

1. Technical Field

The present invention relates to a screening method of high-efficiency biofuel-producing strains by a dielectrophoretic method using vertical nano-gap electrodes and a method of producing biofuel from the screened strains.

2. Description of the Related Art

Biofuels, the most realistic and practical alternative among future transportation energy sources, are expected to occupy a large portion of the market share in 2050, about 27%, and it is necessary to secure an economical production technology therefor. Since 2005, the demand for biodiesel has increased significantly around the world. In particular, in Korea, since 2018, as renewable fuel standard (RFS), a mandatory mixing ratio of biodiesel set at 3%, has been enforced, it is imperative to secure the biodiesel production technology in terms of policy and industry.

As the biodiesel production technology, the second-generation biodiesel production technology based on lignocellulosic biomass having high sustainability and economy has received attention. Particularly, in the case of securing high-efficiency biodiesel-producing microorganisms, which is a core component of second-generation biodiesel production technology, it is determined that it is possible to produce commercial second-generation biodiesel in a short period of time in combination with pre-treatment and/or saccharification technology, which are technologically mature, and it is expected to lead the global biofuel market (on the scale of 82.7 billion USD in 2011, and expected to reach 185.3 billion USD by 2021), which has gradually shifted to second-generation biofuel.

In order to secure high-efficiency biodiesel-producing strains, the development of strains applying various strain design and metabolic engineering techniques has been accelerated, but the screening of developed strains for good strains capable of producing biofuel at a high concentration mainly depends on instrumental analysis using gas chromatography or the like by culturing individual microorganisms in a flask and then extracting lipids. Thus, the number of individuals in a screenable strain candidate group is very limited (less than $10^3$ individuals), and a long time (50 min/individual) is required for the instrumental analysis, thereby limiting an overall rate of developing high-efficiency biofuel-producing microorganisms. In the case of the microorganisms, the number of securable strain candidate groups is high as $10^6$ or more, in the case of securing a system for ultra high-throughput screening (uHTS) capable of more rapidly and efficiently screening the 'high-efficiency biodiesel producing microorganisms', the overall strain development rate may be dramatically improved.

Meanwhile, since the microorganisms may be recognized as particles in a predetermined form having a typical size of several micrometers, application of a conventional particle separation method may be considered. However, since the biofuel-producing microorganisms have similar sizes, it is difficult to apply the separation method according to the size, and since the biofuel-producing microorganisms need to be separated using the difference in properties due to the lipid content, a highly sensitive analyzer is required. In addition, since the microorganisms may be easily damaged by changes in stimulus or environment applied to induce the difference in properties due to the characteristics of cells, it is necessary to find a screening method capable of detecting at high sensitivity under mild conditions.

SUMMARY

The inventors of the present invention have made efforts to develop a method for quickly and easily screening an excellent strain with high lipid content among biofuel-producing microorganisms by applying a dielectrophoresis method without damage due to applied external energy. Using an electrode pair which is constituted by one continuous electrode and the other electrode including an array in which a plurality of holes are patterned while being electrically spaced apart from one electrode through an insulator layer having a thickness of tens to hundreds of nanometers, and which has holes having the same pattern as the electrode formed on the insulator layer, since almost no heat is generated even when low-voltage AC is applied to the electrode pair, it is possible to trap or disperse high-lipid microorganisms selectively due to a minute permittivity difference according to a lipid content difference represented by the microorganism itself at a level that does not cause or minimizes thermal and/or physical damage to the cells by contacting cells to be screened, that is, a fluid containing a microorganism and applying the AC. As a result, the inventors confirmed that excellent, high-efficiency biofuel-producing strains can be rapidly screened from homogeneous microorganism individuals at a high capacity without a separate label such as fluorescence using a large-area electrode pair, thereby completing the present invention.

An aspect of the present invention provides a screening method of biofuel-producing strains including: a first step of contacting an electrode pair by introducing a fluid containing a biofuel-producing strain candidate group to an apparatus contrived so that a dielectrophoretic electrode pair which includes a first conductor electrode; an insulator layer having a constant thickness selected from a range of 5 nm to 1000 nm; and a second conductor electrode stacked sequentially, in which one electrode is continuously formed and the other electrode optionally has one or more holes formed in the same pattern, includes a circuit electrically connected with an AC power supply unit, and the fluid containing a sample is in contact with an electrode surface having holes of the dielectrophoretic electrode pair; a second step of applying an AC voltage to the electrode pair; and a third step of selectively recovering the cells trapped in holes of the electrode pair.

Another aspect of the present invention provides a method of producing biofuel including culturing strains screened by the screening method.

BRIEF DESCRIPTION OF THE DRAWINGS

The above and other objects, features, and advantages of the present invention will be more clearly understood from the following detailed description taken in conjunction with the accompanying drawings, in which.

DETAILED DESCRIPTION

Hereinafter, the present invention will be described in more detail.

In the present invention, when a principle of dielectrophoresis is applied to screen excellent strains having a high lipid content among biofuel-producing microorganisms, in order to exhibit a conventional dielectrophoresis effect, high voltage is required. As a result, due to electrolysis of the accompanying electrolyte, protein denaturation and/or cell damage caused by heat generated in a reaction system using the high voltage, the strains can be separated when applied to the biomaterial. However, in order to overcome a disadvantage that it is limited in that the strains are recovered and used for their original purpose, it is necessary to apply a vertical nano-gap electrode structure including a series of holes formed in a regular pattern capable of exhibiting an excellent dielectric effect even with application of low voltage. Specifically, the electrode structure includes electrodes composed of two conductor films, in which both electrodes are electrically separated from each other by an insulating layer having a thickness of several tens to several hundreds of nanometers, and an electrode pair is formed with a hole array having the same pattern on only one electrode surface and the corresponding insulating layer, and thus, it is possible to cause a dielectrophoresis phenomenon in each hole when alternating voltage is applied to both of the electrodes. Even though low voltage at a sub-V level is applied, the behavior of microorganisms at a micron level is adjusted by properly adjusting a frequency, and due to a difference in permittivity depending on the lipid content of the microorganisms, only excellent strains having a specific lipid content or more are selectively collected in the holes or dispersed into a fluid to be selected from the low-lipid microorganisms.

Figure 1:
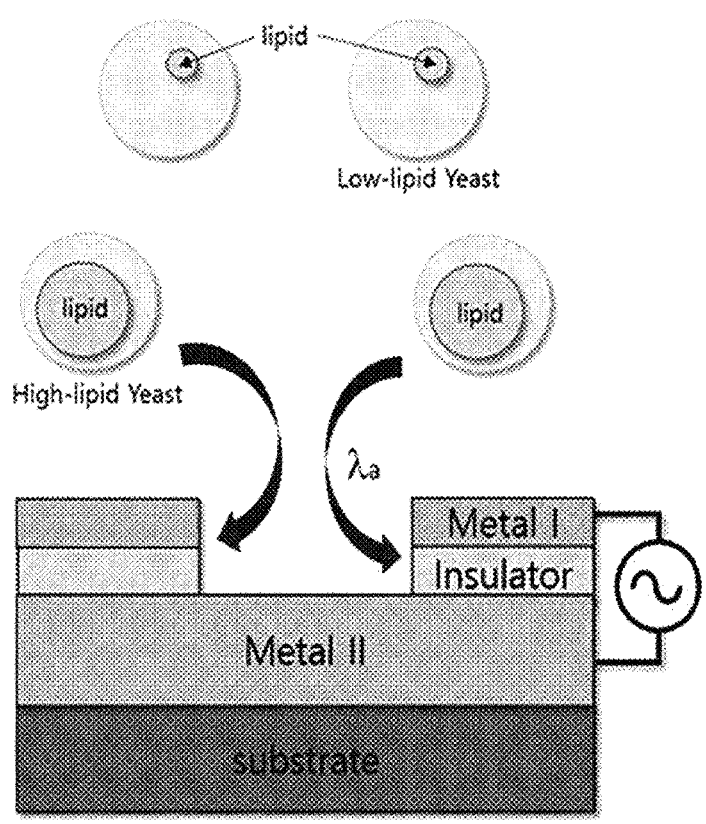
FIG. 1 is a diagram schematically illustrating a principle of selectively collecting a high-lipid yeast strain having high biofuel/material productivity among homogeneous microorganisms by dielectrophoresis (DEP) using a patterned vertical nano-gap electrode according to the present invention.

FIG. 1 schematically illustrates a principle of screening biofuel-producing strains according to a lipid content using dielectrophoresis according to the present invention. The strains having lipid production ability increased by genetic recombination are similar in size and shape to wild-type strains, but exhibit a small difference in permittivity due to the difference in the amount of lipid contained therein, and it is possible to selectively collect and further select microorganisms via the difference in the cell characteristics through the dielectrophoresis using the electrode pair of the present invention. That is, it is possible to control the behavior of the microorganisms adjacent thereto by controlling the frequency applied to the electrode pair, and when a proper frequency of alternating current (AC) is applied, excellent strains having a high lipid content are trapped in the holes of the electrode, and strains having a low lipid content are dispersed into the fluid to separate these strains according to the lipid content.

The present invention relates to a layered structure including a first conductor layer; an insulator layer; and a second conductor layer which are sequentially stacked as an electrode pair, in which the insulating layer has a predetermined thickness selected from a range of 5 nm to 1000 nm, and the first conductor layer is continuous, but the insulator layer and the second conductor layer have one or more holes having the same patterns.

Specifically, the layered structure may be fabricated with a large area of several cm² or more and includes holes formed from at least several to hundreds and at most millions or more by adjusting sizes of the holes included therein and intervals between the holes, thereby controlling microorganisms with equal and/or uniform force and further trapping and/or dispersing a large number of individuals simultaneously according to their characteristics.

For example, the hole may have independently an area of 50 nm² to 10,000 μm², but is not limited thereto. Meanwhile, the hole may have a circular shape, but is not limited thereto. For example, the holes may be formed in various shapes that can be achieved using a nanofabrication technology known in the art.

Being formed in "the same pattern" may mean that the shapes and the sizes of holes included in the insulator layer are the same as each other at a position corresponding thereto, and does not mean that the shapes and the sizes of the entire holes are the same as one another. For example, in one layered structure, at least one hole may be independently the same as each other, or may have a different shape and/or size.

The first conductor layer and the second conductor layer may be films made of the same or different conductive materials.

The layered structure of the present invention is a sandwich-type structure in which a first conductor layer and a second conductor layer, which are electrically conductive, are separated by an insulator layer having a predetermined thickness. The first conductor layer and the second conductor layer may act as parallel electrodes electrically separated through the insulator layer.

Accordingly, the present invention provides a dielectrophoretic electrode pair including a first conductor electrode; an insulator layer; and a second conductor electrode and having holes formed selectively at one side electrode, in which the insulator layer has a predetermined thickness selected in a range of 5 nm to 1000 nm, the first conductor electrode is continuous, but the insulator layer and the second conductor electrode have one or more holes formed in the same pattern.

In the screening method of the present invention, the AC may be applied at a frequency of 10 kHz to 10 MHz and a voltage of 0.1 V to 5 V, but is not limited thereto as long as individuals containing lipid having a content of a predetermined level or more may be selectively collected by applying the AC under a selected condition. Furthermore, it is possible to select a suitable combination at a level that causes a rise in temperature within 2° C. so that there is no damage caused by heat generated due to the characteristic of handling the cells or so that the damage is minimized, but it is limited thereto.

In this case, the cells trapped in the holes may be strains having a relatively high lipid content.

The biofuel-producing strain used in the screening method of the present invention may be a lipid-producing microorganism or a variant thereof. For example, the lipid-producing microorganism may be lipid-producing yeast strains such as *Yarrowia lipolytica, Rhodosporidium toruloides, Lipomyces starkeyi*, and *Trichosporon oleaginosus*; microalgae; or cyanobacteria, but strains capable of producing lipid-based biofuel as the microorganism itself or a genetically modified variant may be used without limitation. The variants of *Yarrowia lipolytica* may be *Yarrowia lipolytica* polf Δpex10, Δmfe1, DGA1 having improved biofuel productivity compared with the wild type through genetic manipulation, but are not limited thereto.

The term "*Yarrowia*" of the present invention refers to a non-pathogenic microorganism of fungal genus belonging to family Dipodascaceae and yeast of monotypic genus including only the species *Yarrowia lipolytica*. The *Yarrowia lipolytica* uses an unusual carbon source such as hydrocarbons, and in particular, is of high interest in industrial microbiology for its application due to its productivity of specialty lipids.

Figure 2:
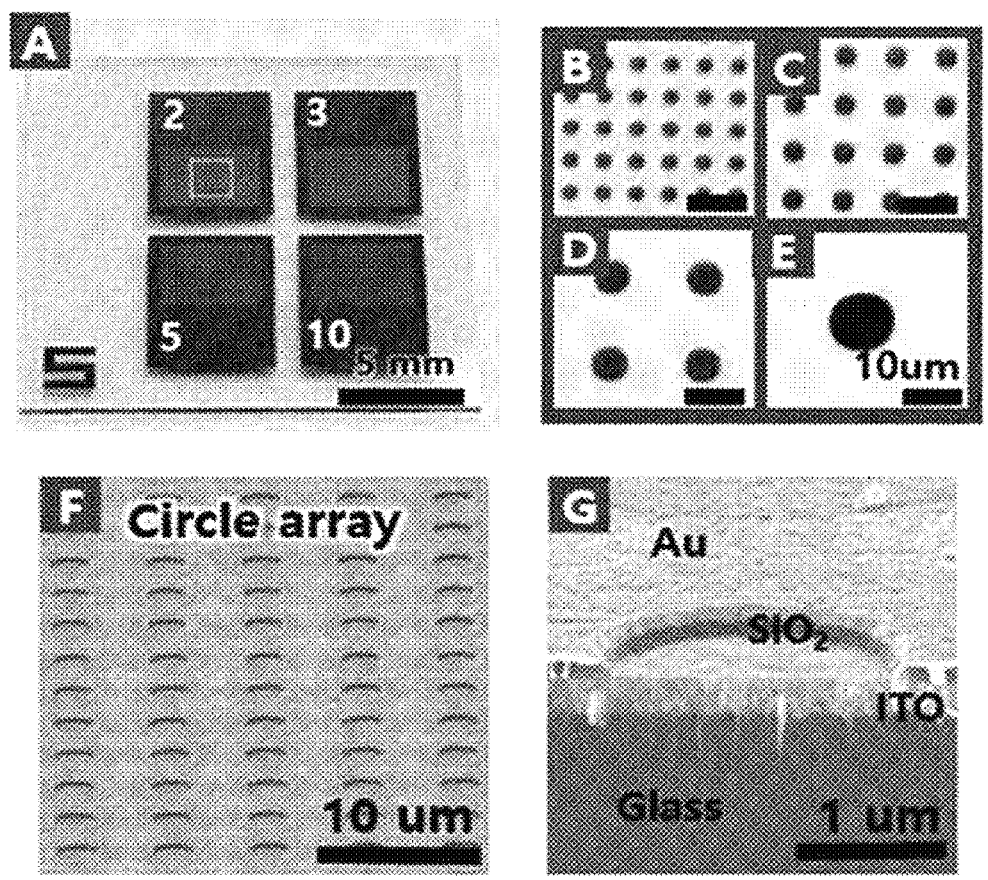
FIG. 2 is a diagram illustrating results obtained by observing shapes and cross sections of a gold electrode including holes formed in patterns of various sizes and a vertical nano-gap electrode formed of an ITO electrode, which are spaced apart from each mm² using the method of the present invention, visually or by a scanning electron microscope (SEM)
Figure 3:
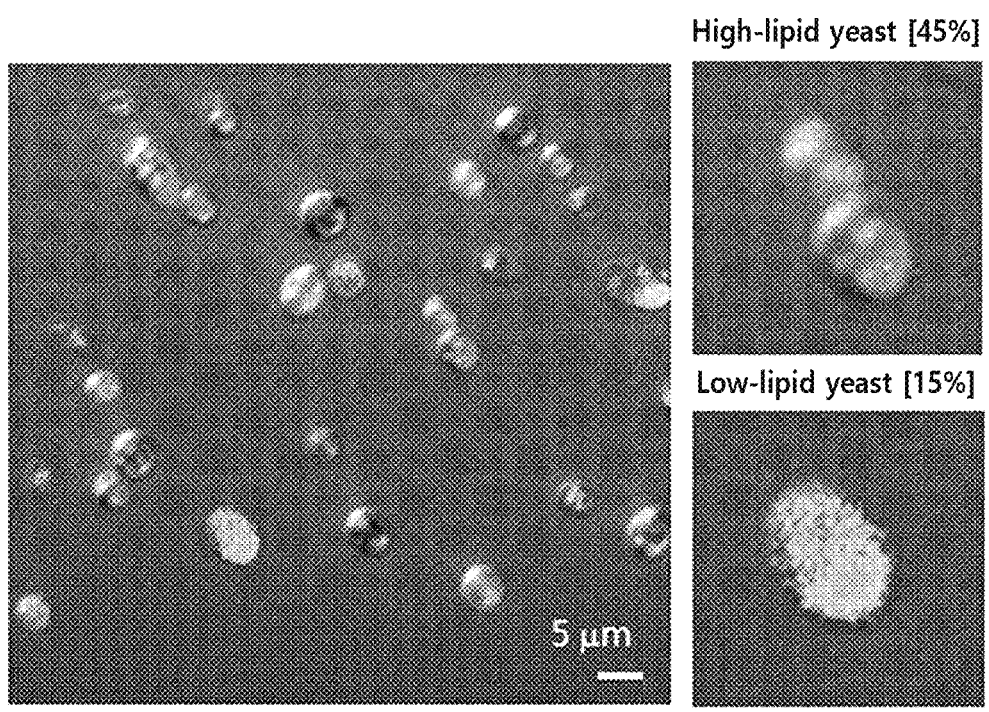
FIG. 3 is a diagram illustrating a confocal microscope image of a high-lipid yeast adjusting the lipid content of the present invention. In order to enable visual identification of yeast strains according to a lipid content on microscopic images, a high-lipid yeast and a low-lipid yeast were labeled to show fluorescence of different colors. Specifically, the high-lipid yeast is labeled to express a red-colored mCherry fluorescence protein, and the whole cells are reddish, and the low-lipid yeast is labeled with green, and the entire cells are green.

In the present invention, the term "dielectrophoresis (DEP)" means a phenomenon in which a force is applied to a dielectric particle when placed in a non-uniform electric field, and the force does not require particle charge and all particles may exhibit dielectrophoretic activity in the presence of an electric field. At this time, the intensity of the applied force, that is, the force of dielectrophoresis ($F_{DEP}$), depends on a frequency of the electric field, the electrical properties of a medium in which the particles are embedded and a particle itself, and the shape and size of the particle. Thus, the electric field at a specific frequency may be used to control particles, e.g., the orientation and/or behavior of the particles. The principle of the dielectrophoresis is illustrated in FIG. 2.

When theoretically describing the dielectrophoresis, the force of dielectrophoresis ($F_{DEP}$) received when a particle is placed in a medium to which AC of frequency ω is applied, for example, a fluid, may be expressed by the following equation.

$$F_{DEP}(\omega) = \pi \varepsilon_m R^3 \cdot \mathrm{Re}(f_{CM}(\omega)) \nabla |E|^2$$

Here, ω is a frequency of the AC applied to the dielectrophoretic electrode pair, $\varepsilon_m$ is the permittivity of the fluid (medium) surrounding the particles, R is a radius of the particle, E is a magnitude of the electric field, and $\mathrm{Re}(f_{CM}(\omega))$ is a real part of the Clausius-Mossotti (CM) function for the frequency of the applied AC. In the above equation, the factor determining the sign of the dielectrophoretic force applied to the particles is the real part of the Clausius-Mossotti (CM) function, which may be calculated according to the following equation.

$$f_{CM}(\omega) = \frac{\varepsilon_p^*(\omega) - \varepsilon_m^*(\omega)}{\varepsilon_p^*(\omega) + 2\varepsilon_m^*(\omega)}$$

Here, ω is a frequency of the AC applied to the dielectrophoretic electrode pair, $\varepsilon^*_p$ is the permittivity of particles to be trapped, and $\varepsilon^*_m$ is the permittivity of the fluid.

When the permittivity of the particles is larger than the permittivity of the medium under the AC of frequency ω, the permittivity has a positive Clausius-Mossotti value, that is, $\mathrm{Re}[f_{CM}]>0$, in which the DEP refers to a positive DEP, and in this state, the particles move toward the larger gradient of the electric field. On the contrary, when the permittivity of the particles is smaller than the permittivity of the medium, the permittivity has a negative Clausius-Mossotti value, that is, $\mathrm{Re}[f_{CM}]<0$, in which the DEP refers to a negative DEP, and in this state, the particles move toward the smaller gradient of the electric field.

The yeast strain to which the screening method of the present invention is applied is a cell having a predetermined shape of several μm in diameter, and thus the cell may be regarded as a kind of particle to generate a dipole. Furthermore, considering the characteristics of dielectrophoresis, even when they are of the same size as the yeast strain, individuals having a high lipid content and individuals having a low lipid content have a difference in degree to form a dipole due to the difference in content of a specific component, particularly, lipids. In other words, even from the same kind of yeast, yeasts having different lipid contents are classified into different kinds of particles from the viewpoint of dielectrophoresis, so that selective collection according to lipid content and selective position control according to lipid content of yeast are possible.

For example, the first conductor electrode and the second conductor electrode may be independently film shapes made of metal selected from the group consisting of copper, gold, silver, platinum, and palladium; alloys or complexes containing at least one metal selected from the group consisting of copper, gold, silver, platinum, and palladium and at least one material selected from the group consisting of tellurium, tungsten, zinc, iridium, ruthenium, arsenic, phosphorus, aluminum, manganese, and silicon; conductive carbon materials selected from the group consisting of graphite, graphene, and derivatives thereof; or mixed metal oxides selected from the group consisting of indium tin oxide (ITO), titanium oxide ($TiO_2$), ruthenium oxide ($RuO_2$), iridium oxide ($IrO_2$), and platinum oxide ($PtO_2$), but are not limited thereto.

The insulator layer may be formed by using a nonconductive material having an insulating property without limitation. For example, the insulator layer may be formed of a metal oxide such as $SiO_2$, $Nb_2O_5$, $TiO_2$, $Al_2O_3$, or MgO, or a polymer such as polyvinylpyrrolidone (PVP), but is not limited thereto. The kind of the material and the thickness of the layer to be formed are not limited as long as the insulator layer may be formed into a uniform thickness at a desired level. However, it is necessary to selectively etch the insulator layer in the manufacturing process due to the morphological characteristics of the electrode pair of the present invention. In this case, the material of the insulator layer may be selected depending on the process to be used, or on the contrary, in the case of selecting a specific material as a material of the insulator layer, the manufacturing process may be designed. For example, when a polymer film is included as the insulator layer, a pattern may be formed by easily etching the polymer film with a corrosive agent, for example, a specific solvent selected depending on a type of polymer.

When the thickness of the insulator layer is thinner than 5 nm, the distance between the first conductor and the second conductor located on both sides of the insulator layer is shorter, and thus the entire layered structure acts as one conductor by a 'tunneling effect' in which electrons are transferred regardless of the presence or absence of the insulator, and the first conductor layer and the second conductor layer are no longer able to function as separate electrodes. Therefore, the thickness of the insulator layer is determined to be the minimum thickness depending on the characteristics of the insulator layer which does not allow the tunneling effect, and this may vary depending on the material of each electrode and the insulator layer to be selected. On the other hand, when the thickness of the insulator layer reaches the micrometer level beyond the nano level, for example, when the thickness of the insulator layer exceeds 1000 nm, the available voltage required for effective particle trapping becomes large, causing bubbles in the fluid and excessive heat generation in a reaction system, and as a result, the dielectrophoretic effect and efficiency and/or sensitivity may be significantly reduced. As described above, the dielectrophoretic effect is a phenomenon caused by a non-uniform electric field. Considering that the electrode pair of the present invention exhibits the dielectrophoretic effect due to a non-uniform electric field formed by one electrode that is a continuous plane and another electrode that has holes formed to be spaced apart from each other in parallel by the nm-level insulator layer, that is, opposing electrodes having different shapes, when the thickness of the insulator layer is increased, the defects due to the holes become relatively small, and as a result, the reduction of the dielectrophoretic effect may be induced. Accordingly, it is apparent to those skilled in the art that the thickness of the insulator layer and/or the size of the hole may be organically controlled in consideration of the size of the particles to be trapped or dispersed which are introduced therein.

In a specific embodiment of the present invention, on an ITO layer having a thickness of 40 nm formed to an area of 4 mm×4 mm, a $SiO_2$ layer having a thickness of 100 nm and a silver layer having a thickness of 100 nm are deposited and then etched to use a electrode pair with an array of periodic patterns in which holes having a diameter of 30 μm are spaced apart from each other at intervals of about 60 μm. An AC voltage of 100 kHz and 1 V is applied to the electrode pair to perform screening of biofuel-producing strains by dielectrophoresis in about 1600 holes at the same time. At this time, the biofuel-producing strains to be separated use *Yarrowia lipolytica*, a wild type of about 10% lipid content, and *Yarrowia lipolytica* polf Δpex10, Δmfe1, and DGA1 variants having about 50% lipid content, which are increased in lipid production by gene recombination, and individuals of variants with increased lipid content are selectively collected in the holes.

In addition, the present invention may produce the biofuel through a step of culturing the screened strain by the above-mentioned method. The screened strain may be the cells selectively recovered from the third step of the above-mentioned method.

At this time, in the culturing, as the carbon source, saccharides such as glucose, fructose, galactose, and mannose; fatty acids such as oleic acid; alcohols such as glycerol and ethanol and organic acids such as acetic acid and the like are supplied to obtain lipids such as palmitic acid, palmitoleic acid, hexadecadienoic acid, stearic acid, oleic acid, and linolenic acid. These lipids may be converted through transesterification and used as biofuel, or may be used as cosmetic raw materials and food materials themselves.

For the production of high-efficiency biofuel, the strain may use screened individuals having lipid productivity of 20% or more of dry cell weight (DCW). Specifically, individuals having productivity of DCW of 30% or more, more specifically 40% or more, may be used, but the present invention is not limited thereto. The strain used in the biofuel production method of the present invention may be individuals screened to have a fat content equal to or higher than a desired content, that is, to have a desired level of lipid productivity by the screening method using dielectrophoresis described above.

The layered structure and the dielectrophoretic electrode pair according to the present invention may be manufactured by a process including a first step of preparing the layered structure including a first conductor layer, an insulator layer having a constant thickness selected from a range of 5 nm to 1000 nm, a second conductor layer, and a photosensitive resin layer contrived with a desired pattern; a second step of selectively etching the insulator layer, the second conductor layer, and the photosensitive resin layer according to the contrived pattern by etching; and a third step of removing the remaining photosensitive resin layer. For example, the manufacturing method may be performed by combining stacking and etching methods of various materials known in the art. The detailed method of performing each step may be selected according to a material of each selected layer.

For example, etching may be performed using a dry and/or wet etching method. In the case where each constituent layer is formed of a known material and thickness, a dry etching method may be selected, and the execution time may be determined in consideration of an etching rate of each layer according to a selected method. On the other hand, when the insulator layer includes a polymer film such as PVP, the wet etching method may be selected in consideration of the fact that only the corresponding polymer film may be selectively removed by a simple method of treating with a specific solvent (etchant). Alternatively, if necessary, a combined method may be used in which the second conductor layer is etched by a dry etching method and the insulator layer is etched by a wet etching method, but the present invention is not limited thereto. The etching method may be selected by complexly considering the material of each constituent layer, the etching method known in the art, and/or the convenience and economical efficiency of the process performance.

Further, another method for manufacturing a layered structure and a dielectrophoretic electrode pair according to the present invention may include a first step of preparing a layered structure including a first conductor layer, an insulator layer having a constant thickness selected from a range of 5 nm to 1000 nm, a photosensitive resin layer contrived with a pattern; a second step of forming a second conductor layer on the layered structure to be spaced apart from the first conductor layer by the insulator layer and the photosensitive resin layer; and a third step of forming a structure added with the second conductor layer formed with a pattern having an opposite image to the pattern of the photosensitive resin layer on the layered structure in which the first conductor layer and the insulator layer are sequentially stacked. At this time, the layered structure of the first step may be stacked in the order of the first conductor layer, the insulator layer, and the photosensitive resin layer, or in the order of the first conductor layer, the photosensitive resin layer, and the insulator layer.

In the manufacturing method, in the case of using the layered structure which is stacked in the order of the first conductor layer, the insulator layer, and the photosensitive resin layer in the first step, the method may further include a fourth step of selectively etching the insulator layer to have the same pattern as the second conductor layer by etching after the third step. In the etching process, the patterned second conductor layer formed on the insulator layer may act as a mask. The fourth step may be performed using a dry or wet etching method known in the art.

In the screening method of the biofuel-producing strains, the selective collection of strains to be desired or excluded may be achieved by using a method including a first step of deriving a Clausius-Mossotti (CM) curve according to the applied AC frequency for the strains to be trapped using the following equation 1; and a second step of applying AC of a frequency selected in a range in which a real part of the Clausius-Mossotti in the curve derived from the first step represents a positive value:

$$f_{CM}(\omega) = \frac{\varepsilon_p^*(\omega) - \varepsilon_m^*(\omega)}{\varepsilon_p^*(\omega) + 2\varepsilon_m^*(\omega)} \quad \text{[Equation 1]}$$

In Equation 1 above,
$\omega$ is a frequency of the AC applied to the dielectrophoretic electrode pair,
$\varepsilon_p^*$ is permittivity of the strain to be trapped, and
$\varepsilon_m^*$ is permittivity of the fluid.

Further, according to the present invention, the dielectrophoretic electrode pair having holes selectively formed on one side electrode includes a circuit electrically connected to an AC supply unit, and using an apparatus contrived so that an electrode surface formed with the holes of the dielectrophoretic electrode pair contacts a fluid including a sample, as a principle similar to the particle trapping method described above, it may be used to select specific biofuel-producing strains, for example, strains having a predetermined level or more of lipid content, or exclude strains having less than the predetermined level of lipid content from a mixture including N (a natural number of 2 or more) kinds of biofuel-producing strains in the fluid.

Particularly, the screening method may be achieved by a method including a first step of deriving a Clausius-Mossotti curve according to a frequency of individual strains to be separated, for example, biofuel-producing strains having different lipid contents, using Equation 1-1 below; a second step of selecting frequencies having a real part of the Clausius-Mossotti which is a positive or negative value for some biofuel-producing strain(s) and an opposite value for other particle(s) to be separated, from the curved derived from the first step; and a third step of applying the AC of the frequency selected from the second step:

$$f_{CM_n}(\omega) = \frac{\varepsilon_{p_n}^*(\omega) - \varepsilon_m^*(\omega)}{\varepsilon_{p_n}^*(\omega) + 2\varepsilon_m^*(\omega)} \quad \text{[Equation 1-1]}$$

In Equation 1-1 above,
$\omega$ is a frequency of the AC applied to the dielectrophoretic electrode pair,
N is an arbitrary number for distinguishing a kind of particle, a natural number of $1 \leq n \leq N$,
$\varepsilon_{p_n}^*$ is permittivity of biofuel-producing strain n, and
$\varepsilon_m^*$ is permittivity of the fluid.

Furthermore, the screening method of the biofuel-producing strains of the present invention may be performed by repeating the second step and the third step one or more times with respect to the biofuel-producing strain(s) trapped or excluded in the third step, but is not limited thereto.

The repeating step in the screening method of the biofuel-producing strains of the present invention is performed by changing the frequency of the applied AC, and may be continuously performed using an apparatus used for primary separation as it is or using the same apparatus connected thereto in parallel. For example, after separation of excellent strains or bad strains from the primary biofuel-producing strains, when two or more kinds of biofuel-producing strains including biofuel-producing strains of interest are left in the holes to separate the biofuel-producing strains of interest from those producing biofuel-producing strains, the biofuel-producing strains dispersed in the fluid other than the biofuel-producing strains trapped in the holes after the primary separation are removed. Thereafter, while a fresh fluid having the same permittivity is filled and AC having a frequency different from the primary separation is applied to the same apparatus or a fluid having permittivity different from the primary separation is filled and the frequency is maintained, repeated separation may be performed. Alternatively, in the case where the biofuel-producing strains of interest to be separated are not trapped in the holes in the primary separation, but are dispersed together with other biofuel-producing strains in the fluid, a process of transmitting the fluid containing the biofuel-producing strains of interest to a novel separation apparatus including the dielectrophoretic electrode pair of the present invention connected thereto and separating mixed stains in the same manner by applying a changed frequency to the novel separation apparatus may be repeatedly performed.

According to the present invention, since one electrode has a series of patterned holes selectively formed and an electrode pair separated by a vertical nano-gap formed by the insulator layer is used to selectively collect particles having a specific property by a dielectrophoretic effect in the plurality of holes at the same time, based on the phenomenon, the present invention can be usefully applied to screen excellent, high-lipid yeast strains having similar sizes and different lipid contents from low-lipid yeast.

DESCRIPTION OF THE PREFERRED EMBODIMENTS

Hereinafter, the present invention will be described in more detail with reference to Examples. However, these Examples are only illustrative of the present invention, and the scope of the present invention is not limited to these Examples.

Preparation Example 1: Manufacture of Large-Area Vertical Nano-Gap Array of which One Surface has Patterned Holes and Both Surfaces are Spaced Apart from Each Other by $SiO_2$ An ITO layer was formed on a glass substrate patterned with an area of 1 cm×1 cm at a thickness of 40 nm and an area of 4 mm×4 mm and then a $SiO_2$ layer was deposited at a thickness of 100 nm using a plasma-enhanced chemical vapor deposition (PECVD) apparatus. Thereafter, a silver layer of a thickness of 100 nm was formed on the $SiO_2$ layer by a thermal evaporator. Subsequently, a photosensitive resin (AZ152, Microchemical) was spin-coated and heated to form a photosensitive resin layer. A photomask having a pattern in an array form in which a series of holes having a diameter of 30 μm were arranged at intervals of 30 μm was positioned on the surface with the photosensitive resin layer and ultraviolet light was irradiated on the photomask and then developed to remove the masked portion. As described above, inductively coupled plasma (ICP) etching was performed on the layered structure in which the hole array pattern was formed of the photosensitive resin to etch the second conductor layer and the insulator layer exposed at the lower end of the hole pattern in the same shape as the pattern. The etching rates during etching by the ICP etching are different from each other in gold constituting the second conductor layer and $SiO_2$ constituting the insulator layer, and the treatment time was calculated by considering the thickness of each layer and the etching rate for the material so that the first insulator layer was maintained and the second conductor layer and the insulator layer may be selectively removed. In particular, in the case of $SiO_2$ etching by the ICP etching, the etching was performed at pressure of 4 mTorr under 15 sccm of argon gas and 90 sccm of $CHF_3$ gas, and with ICP 2770 W and bias 75 W at pressure of helium 5 mTorr for about 230 nm/sec. On the other hand, in the case of the silver layer, the etching was performed at pressure of 0.5 Torr under 8 sccm of argon gas and 4 sccm of $Cl_2$ gas, and with ICP 1000 W and bias 150 W at pressure of helium 5 mTorr for about 130 nm/sec.

Preparation Example 2: Manufacture of Large-Area Vertical Nano-Gap Array of which One Surface has Patterned Holes and Both Surfaces are Spaced Apart from Each Other by PVP A polyvinylphenol (PVP) solution was spin-coated on a glass substrate patterned with a 180 nm-thick ITO layer of an area of 1 cm×1 cm and heated to form a 110 nm-thick insulator layer made of PVP. Subsequently, a photosensitive resin (AZ1512) was spin-coated on the PVP layer and heated to form a photosensitive resin layer. A photomask having a pattern in an array form in which a series of holes having a diameter of 30 μm were arranged at intervals of 30 μm was positioned on the surface with the photosensitive resin layer and ultraviolet light was irradiated on the photomask and then developed to remove the masked portion. A 120 nm-thick gold thin film was formed on the patterned surface of the laminated structure including the patterned photosensitive resin layer by a thermal evaporation method. Thereafter, the remaining photosensitive resin pattern and the unnecessary gold thin film formed on the surface thereof were removed by treatment with acetone to obtain a gold thin film layer having a pattern in a hole array form. Furthermore, the patterned gold thin film was used as a mask by treatment at 150 W for 2 minutes and 15 seconds through reactive ion etching using oxygen gas at a flow rate of 100 sccm at a pressure of 100 mTorr to selectively remove a portion of the PVP insulator layer exposed to the hole portion which was not covered by the gold thin film.

Preparation Example 3: Manufacture of High-Efficiency Biofuel-Producing Strains In order to manufacture high-efficiency biofuel-producing strains, *Yarrowia lipolytica* was used as a basic strain. A wild-type of *Yarrowia lipolytica* POlf (about 10% of lipid content) was used as a low-lipid microorganism and variants *Yarrowia lipolytica* polf Δpex10, Δmfe1, DGA1 (lipid content of about 50%) produced by genetic recombination were used as a high-lipid microorganism. The two kinds of strains were cultured in a yeast synthetic complete (YSC) medium including glucose (50 g/L), a yeast nitrogen base (YNB) (MPbio, 1.7 g/L), ammonium sulfate (2.2 g/L), and complete supplement mixture without uracil (CSM-Leu, Becton Dickinson and Company, 0.67 g/L).

For the inoculation of two kinds of strains having different lipid contents, seed culture was performed for 48 hours in 3 mL of a medium, 500 μL of the seed culture was transferred to 10 mL of a fresh YSC medium and pre-cultured for 24 hours. For the main culture, the pre-cultured strains were inoculated into a 250 mL flask containing 25 mL of the YSC medium with an initial inoculation amount of $OD_{600}$ 0.2 unit (1 to $4\times10^6$ cells/mL) to accumulate lipids in the strains. In all the culturing steps, the incubator was maintained under conditions of 200 rpm and 28° C. After the culture, the strains were harvested by centrifugation at 500 g for 2 minutes, and the remaining medium was completely removed by re-suspending the strains twice with distilled water for application to dielectrophoretic screening.

Preparation Example 4: Manufacture of Fluorescently Labeled Yeast Cells

Thereafter, yeast cells were fluorescently labeled so that information of the cells separated using the array of the present invention can be visually confirmed. Specifically, a plasmid capable of expressing a fluorescent protein was prepared and expressed. As the fluorescent protein, a red-colored mCherry fluorescent protein that absorbs light at a wavelength of 587 nm and emits light at a wavelength of 610 nm was selected. A TEF promoter capable of constantly being expressed was used for expression of the mCherry fluorescent protein. The prepared expression vector was transformed into yeast capable of producing a high concentration of lipid to obtain strains fluorescently labeled to exhibit red fluorescence.

Experimental Example 1: Shape Analysis of Vertical Nano-Gap Array

According to the Preparation Examples 1 and 2, an electrode pair including one electrode formed continuously and the other electrode formed with a plurality of hole array patterns, which were manufactured at areas of several $mm^2$ and several cm², respectively, and spaced apart from each other by a nano-gap formed of an insulator, was illustrated in FIG. 2. An outer shape of the electrode pair manufactured above was observed visually (FIG. 2A), a part patterned with different sizes was observed by a microscope (FIGS. 2B to 2E), and a fine hole array pattern and a cross section were confirmed by SEM and illustrated in FIGS. 2F and 2G.

Example 1: Trapping and Dispersion of Yeast Using Dielectrophoretic Method

In the present invention, to confirm applicability for detection of biological materials of the electrode pair prepared according to the Preparation Examples 1 and 2, a solution containing microbial yeast was applied to the electrode pair and whether to trap yeast by the electrode was confirmed.

First, before an actual experiment, a dielectrophoresis phenomenon was predicted through simulation. The force acting on the particles by the dielectrophoresis is determined by the conductivity of the material surrounding the particles, the permittivity, and the frequency of the applied AC voltage and may be calculated according to the following equation.

$$F_{DEP}(\omega) = \pi\varepsilon_m R^3 \cdot \text{Re}(f_{CM}(\omega))\nabla|E|^2$$

Here, $\omega$ is a frequency of AC applied to the dielectrophoretic electrode pair, $\varepsilon_m$ is the permittivity of the fluid (medium) surrounding the particles, R is a radius of the used particle, E is a magnitude of the electric field, and $\text{Re}(f_{CM}(\omega))$ is a real part of the Clausius-Mossotti (CM) function for the frequency of the applied AC. In the above equation, the factor determining the sign of the dielectrophoretic force applied to the particles is the real part of the Clausius-Mossotti (CM) function, which may be calculated according to the following equation.

$$f_{CM}(\omega) = \frac{\varepsilon_p^*(\omega) - \varepsilon_m^*(\omega)}{\varepsilon_p^*(\omega) + 2\varepsilon_m^*(\omega)}$$

Figure 4A:
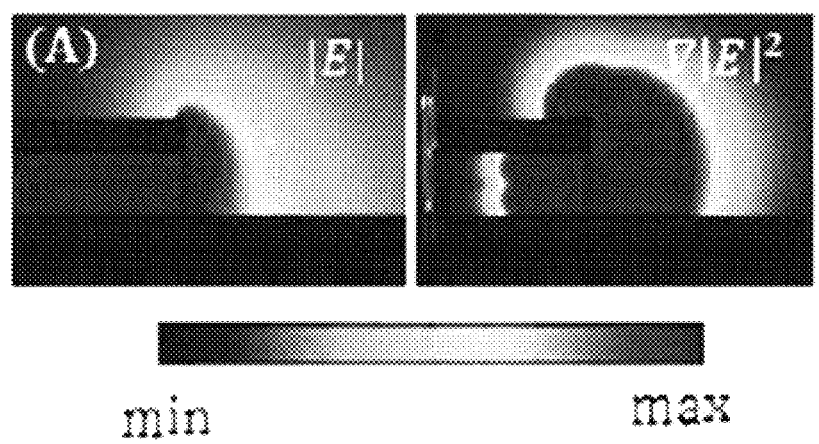
FIG. 4A is a diagram illustrating an electric field distribution in an electrode pair (patterned gold and ITO) spaced apart from each other by PVP as a conductor layer according to an embodiment of the present invention.

Here, $\omega$ is a frequency of the AC applied to the dielectrophoretic electrode pair, $\varepsilon^*_p$ is the permittivity of particles to be captured, and $\varepsilon^*_m$ is the permittivity of the fluid. When an AC voltage is applied to the dielectrophoretic electrode pair prepared according to Preparation Examples 1 and 2, distribution of an electric field to be generated was illustrated in FIG. 4A and the Clausius-Mossotti (CM) function according to the frequency for the yeast having a size of 10 $\mu$m derived theoretically from the equation was illustrated in FIG. 4B. In the case of the yeast, a Clausius-Mossotti value calculated by substituting the value obtained from the literature value shows that the characteristic thereof is changed based on 1 MHz, and specifically, shows a positive value at a frequency of less than 1 MHz and a negative value at a frequency exceeding 1 MHz.

Figure 4B:
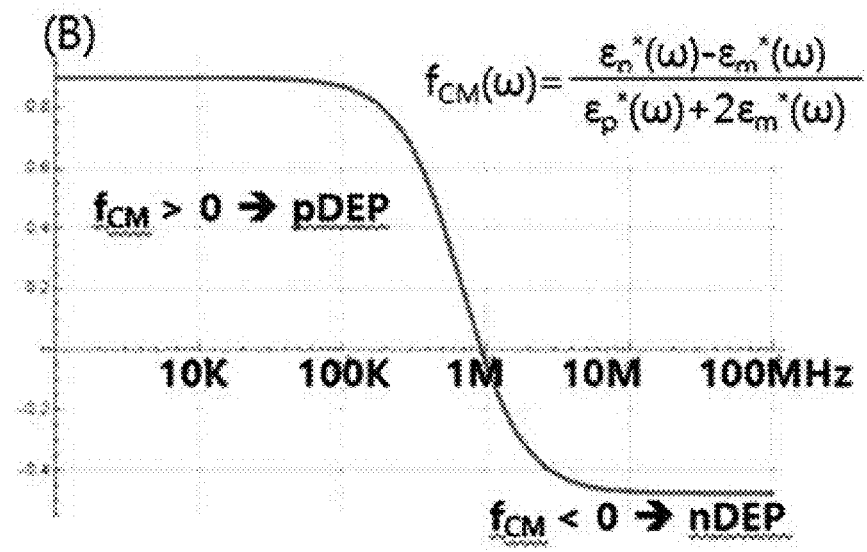
FIG. 4B is a diagram illustrating a Clausius-Mossotti curve according to a frequency derived by simulation with respect to polystyrene particles (diameter of 7 μm) as a yeast strain mimic having a similar size. The Clausius-Mossotti curve is illustrated with respect to two kinds of cells of a low-lipid yeast (10%) and a high-lipid yeast (50%) and a movement direction of each cell may be determined by a Clausius-Mossotti value according to the frequency of these two kinds of strains. Therefore, in order to make these strains have different directions of motion, frequencies are selected so that each Clausius-Mossotti value is in the negative and positive regions.

From the graph of FIG. 4B, when the dielectrophoretic force applied to the particles upon application of the AC voltage calculated through the two equations is associated with the movement of the particles, it was expected that the particles receiving the positive dielectrophoretic force move toward the electrodes, while particles receiving the negative dielectrophoretic force move in the reverse direction of the electrodes.

In order to confirm whether the result predicted by the theoretical calculation can actually be realized by using the dielectrophoretic electrode pair according to the present invention, on the surface formed with the hole array pattern of the electrode pair manufactured according to Preparation Examples 1 and 2, a device is constructed to be in contact with a fluid (tertiary distilled water of 18.2 M$\Omega$ or more) containing yeast having a diameter of 10 $\mu$m and an AC power source is connected to two electrodes electrically connected to each other to induce dielectrophoresis, and then the behavior of particles in the fluid according to the AC frequency was checked by video. Specifically, a voltage of 100 kHz, 1 V was applied to an apparatus provided with an electrode pair manufactured according to Preparation Example 1 in contact with the fluid containing the yeast, and then the behavior of yeast was measured and the results were illustrated in FIG. 5.

Figure 5:
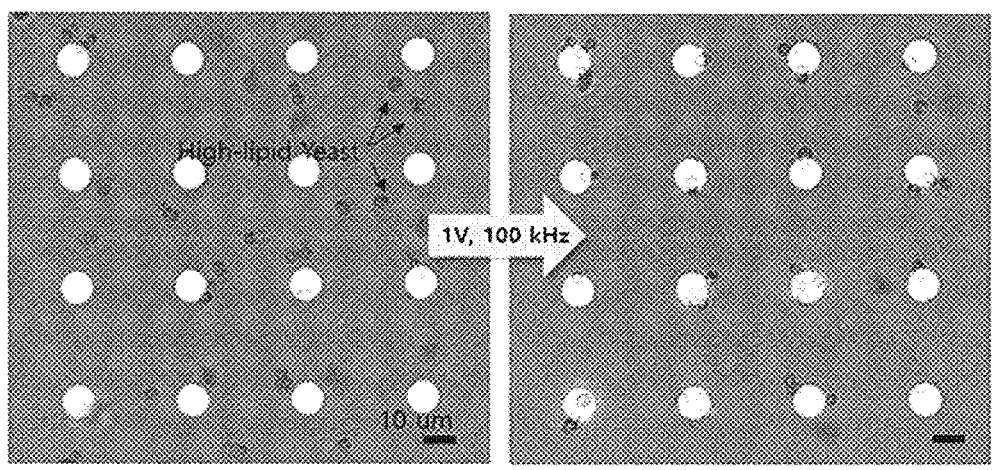
FIG. 5 is a diagram illustrating a microscope image observed in a transmission mode before and after applying an AC voltage of 1 V at a frequency of 100 kHz in which the Clausius-Mossotti value of the calculated curve is selected in a positive region and a negative region. The high-lipid yeast (50%) uniformly or randomly floated on the prepared electrode is immediately trapped into the electrode and trapped at the edge portion of the electrode pattern as the AC voltage is applied.

As illustrated in FIG. 5, when AC of 100 kHz having a positive Clausius-Mossotti value is applied, the yeast was trapped in the holes by receiving the dielectrophoretic force in the direction facing the electrode and arranged along an edge of the holes to be adjacent to the electrode.

Figure 6:
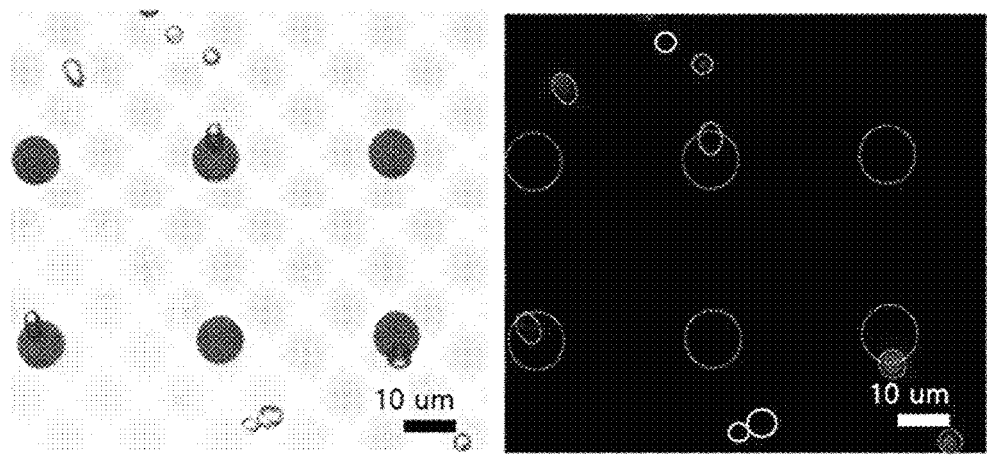
FIG. 6 is a diagram illustrating an optical image (left) and a fluorescent image (right) corresponding thereto of yeast trapped in holes of an electrode, in the case where two kinds of yeast strains containing lipids having the same size and different contents (50% and 10%) are mixed at the same amount and then diluted with distilled water to be a $OD_{600}$ unit 1 (0.5 to 2×10⁷ cells/mL), and divided on the electrode, and then an AC voltage of 0.5 V is applied at a frequency of 100 kHz. In order to distinguish the difference in lipid content from the fluorescence labeling, a fluorescence image confirmed by using a red filter (EX 542-582/EM 604-644) shows that the high-lipid yeast labeled with mCherry fluorescence is selectively collected in the electrode.

Example 2: Selective Separation of Yeast According to Fat Content Using Dielectrophoretic Method Further, in order to verify the possibility of selective separation of yeast according to the fat content using an electrode pair including one electrode formed continuously and the other electrode formed with a plurality of hole array patterns, which are spaced apart from each other by a nano-gap formed of an insulator according to the present invention, a low-lipid (15%) yeast was mixed with a high-lipid (50%) yeast labeled with mCherry according to Preparation Example 3 in the same ratio and then diluted with tertiary distilled water, added onto the prepared electrode at a concentration between $OD_{600}$ 0.2 to 1 unit, and applied with a voltage of 100 kHz and 1 V, and then observed by optical and fluorescence microscopes to obtain images (FIGS. 5 and 6). The corresponding experiment was performed on an electrode of an array pattern formed with holes having a diameter of 30 $\mu$m spaced apart from each other at intervals of 60 $\mu$m, and a voltage of 100 kHz and 1 V was simultaneously to two electrodes vertically arranged through a hole pattern periodically arranged at 4 mm×4 mm to operate simultaneously in about 1600 holes.

The obtained optical and fluorescence microscopic images were superimposed on each other to identify the kind of yeast trapped in the holes of the electrode pair. As a result, it was found that only the high-lipid yeast stained with mCherry was selectively collected. This is because the electrode pair manufactured according to the present invention can trap and concentrate particles by the dielectrophoretic force at a low voltage and further separate and/or purify the yeast according to the size and/or the lipid content (that is, different permittivity) by the principle to have a great potential. Since the larger lipid content is largely influenced by dielectrophoretic force, it is confirmed that the excellent yeast strain having the highest level lipid content is selectively separated from homogeneous yeast strains having various lipid contents, thereby accurately and rapidly screening the excellent strains from a large amount of yeast strains in the future.

What is claimed is:

1. A screening method of biofuel-producing strains comprising:
   a first step of introducing a fluid containing a biofuel-producing strain candidate group to an apparatus including a layered structure including a first conductor 1. layer; an insulator layer having a constant thickness selected from a range of 5 nm to 1000 nm; and a second conductor layer which are stacked sequentially as a dielectrophoretic electrode pair and a circuit electrically connected with an AC power supply unit, in which holes commonly penetrating both the insulator layer and the second conductor layer are defined in the insulator layer and the second conductor layer in a regular pattern, a shape and a size of part of the hole included in the insulator layer are the same as a shape and a size of part of the hole included in the second conductor layer at a corresponding position, and the first conductor layer is continuous and does not have a hole at the corresponding position, and disposing the fluid to contact with an upper surface of the first conductor layer and inside the holes;

a second step of applying an AC voltage between the first conductor layer and the second conductor layer; and a third step of selectively recovering cells trapped in holes of the electrode pair.

2. The screening method of claim 1, wherein the holes have each independently an area of 50 nm$^2$ to 10,000 μm$^2$.

3. The screening method of claim 1, wherein the AC derives a Clausius-Mossotti (CM) curve according to an applied AC frequency with respect to a strain to be trapped using Equation 1 below and has a frequency selected in a range where a real part of the Clausius-Mossotti in the derived curve is a positive value:

$$f_{CM}(\omega) = \frac{\varepsilon_p^*(\omega) - \varepsilon_m^*(\omega)}{\varepsilon_p^*(\omega) + 2\varepsilon_m^*(\omega)} \quad \text{[Equation 1]}$$

in Equation above, $\omega$ is a frequency of the AC applied to the dielectrophoretic electrode pair, $\varepsilon_p^*$ is the permittivity of the particles to be trapped, and $\varepsilon_m^*$ is the permittivity of the fluid.

4. The screening method of claim 1, wherein the AC is applied at a frequency of 10 kHz to 10 MHz and a voltage of 0.1 V to 5 V.

5. The screening method of claim 1, wherein the cells trapped in the holes in the third step are strains having a relatively high lipid content.

6. The screening method of claim 1, wherein the biofuel-producing strain is a lipid-producing microorganism or a variant thereof.

7. The screening method of claim 1, wherein the first conductor layer and the second conductor layer are each independently made of metal selected from the group consisting of copper, gold, silver, platinum, and palladium; alloys or complexes containing at least one metal selected from the group consisting of copper, gold, silver, platinum, and palladium and at least one material selected from the group consisting of tellurium, tungsten, zinc, iridium, ruthenium, arsenic, phosphorus, aluminum, manganese, and silicon; conductive carbon materials selected from the group consisting of graphite, graphene, and derivatives thereof; or mixed metal oxides selected from the group consisting of indium tin oxide (ITO), titanium oxide ($TiO_2$), ruthenium oxide ($RuO_2$), iridium oxide ($IrO_2$), and platinum oxide ($PtO_2$).

8. The screening method of claim 1, wherein the insulator layer is made of a material selected from the group consisting of $SiO_2$, polyvinylpyrrolidone (PVP), $Nb_2O_5$, $TiO_2$, $Al_2O_3$, and MgO.

9. A producing method of biofuel comprising:

a first step of introducing a fluid containing a biofuel-producing strain candidate group to an apparatus including a layered structure including a first conductor layer; an insulator layer having a constant thickness selected from a range of 5 nm to 1000 nm; and a second conductor layer which are stacked sequentially as a dielectrophoretic electrode pair, and a circuit electrically connected with an AC power supply unit, in which holes commonly penetrating both the insulator layer and the second conductor layer are defined in the insular layer and the second conductor layer in a regular pattern, a shape and a size of part of the hole included in the insulator layer are the same as a shape and a size of part of the hole included in the second conductor layer at a corresponding position, and the first conductor layer in continuous and does not have a hole in the corresponding position, and disposing the fluid to contact with an upper surface of the first conductor layer and inside the holes;

a second step of applying an AC voltage between the first conductor layer and the second conductor layer;

a third step of selectively recovering cells trapped in holes of the electrode pair; and a fourth step of culturing the cells selectively recovered from the third step.

10. The producing method of claim 9, wherein the holes have each independently an area of 50 nm$^2$ to 10,000 μm$^2$.

11. The producing method of claim 9, wherein the AC derives a Clausius-Mossotti (CM) curve according to an applied AC frequency with respect to a strain to be trapped using Equation 1 below and has a frequency selected in a range where a real part of the Clausius-Mossotti in the derived curve is a positive value:

$$f_{CM}(\omega) = \frac{\varepsilon_p^*(\omega) - \varepsilon_m^*(\omega)}{\varepsilon_p^*(\omega) + 2\varepsilon_m^*(\omega)} \quad \text{[Equation 1]}$$

in Equation above, $\omega$ is a frequency of the AC applied to the dielectrophoretic electrode pair, $\varepsilon^{*p}$ is the permittivity of the particles to be trapped, and $\varepsilon_m^*$ is the permittivity of the fluid.

12. The producing method of claim 9, wherein the AC is applied at a frequency of 10 kHz to 10 MHz and a voltage of 0.1 V to 5 V.

13. The producing method of claim 9, wherein the cells trapped in the holes in the third step are strains having a relatively high lipid content.

14. The producing method of claim 9, wherein the biofuel-producing strain is a lipid-producing microorganism or a variant thereof.

15. The producing method of claim 9, wherein the first conductor layer and the second conductor layer are each independently made of metal selected from the group consisting of copper, gold, silver, platinum, and palladium; alloys or complexes containing at least one metal selected from the group consisting of copper, gold, silver, platinum, and palladium and at least one material selected from the group consisting of tellurium, tungsten, zinc, iridium, ruthenium, arsenic, phosphorus, aluminum, manganese, and silicon; conductive carbon materials selected from the group consisting of graphite, graphene, and derivatives thereof; or mixed metal oxides selected from the group consisting of indium tin oxide (ITO), titanium oxide ($TiO_2$), ruthenium oxide ($RuO_2$), iridium oxide ($IrO_2$), and platinum oxide ($PtO_2$).

16. The producing method of claim 9, wherein the insulator layer is made of a material selected from the group consisting of $SiO_2$, polyvinylpyrrolidone (PVP), $Nb_2O_5$, $TiO_2$, $Al_2O_3$, and MgO.

17. The producing method of claim 9, wherein as the carbon source, at least one material selected from the group consisting of saccharides such as glucose, fructose, galactose, and mannose; fatty acids such as oleic acid; alcohols such as glycerol and ethanol and organic acids such as acetic acid and the like is supplied to obtain at least one lipid selected from the group consisting of palmitic acid, palmitoleic acid, hexadecadienoic acid, stearic acid, oleic acid, and linolenic acid.

18. The producing method of claim 9, wherein the strain has lipid productivity of 20% or more of dry well weight (DCW).

19. An apparatus for screening biofuel-producing strains comprising:
   a layered structure including a first conductor layer, an insulator layer, and a second conductor layer which are sequentially stacked as a dielectrophoretic electrode pair,
   wherein the insulating layer has a thickness of 5 nm to 1000 nm,
   holes commonly penetrating both the insulator layer and the second conductor layer are defined in the insulator layer and the second conductor layer in a regular pattern,
   a shape and a size of part of the hole included in the insulator layer are the same as a shape and a size of part of the hole included in the second conductor layer at a corresponding position,
   the first conductor layer is continuous and does not have a hole at the corresponding position,
   an AC voltage is applied between the first conductor layer and the second conductor layer, and
   the apparatus further includes a chamber above the first conductor layer so that a fluid containing a biofuel-producing strain candidate group is introduced in the chamber and disposed in contact with an upper surface of the first conductor layer and inside the holes.

* * * * *